(12) United States Patent
Shavit

(10) Patent No.: US 9,943,469 B2
(45) Date of Patent: Apr. 17, 2018

(54) SCENTED BODY COMPOSITIONS

(71) Applicant: MAORI S.C. LTD., Tel Aviv (IL)

(72) Inventor: Shoval Shavit, Tel Aviv (IL)

(73) Assignee: MAORI S.C. LTD., Tel Aviv (IL)

( * ) Notice: Subject to any disclaimer, the term of this patent is extended or adjusted under 35 U.S.C. 154(b) by 0 days.

(21) Appl. No.: 15/112,219

(22) PCT Filed: Jan. 22, 2015

(86) PCT No.: PCT/IL2015/050088
§ 371 (c)(1),
(2) Date: Jul. 18, 2016

(87) PCT Pub. No.: WO2015/111060
PCT Pub. Date: Jul. 30, 2015

(65) Prior Publication Data
US 2016/0338915 A1 Nov. 24, 2016

Related U.S. Application Data

(60) Provisional application No. 61/930,539, filed on Jan. 23, 2014.

(51) Int. Cl.
| *A61L 9/04* | (2006.01) |
| *A61K 8/00* | (2006.01) |
| *A61K 8/11* | (2006.01) |
| *A61K 8/26* | (2006.01) |
| *A61Q 13/00* | (2006.01) |
| *A61K 8/73* | (2006.01) |
| *A61K 8/81* | (2006.01) |

(52) U.S. Cl.
CPC ............... *A61K 8/11* (2013.01); *A61K 8/26* (2013.01); *A61K 8/731* (2013.01); *A61K 8/8152* (2013.01); *A61Q 13/00* (2013.01); *A61K 2800/48* (2013.01); *A61K 2800/52* (2013.01); *A61K 2800/56* (2013.01); *A61K 2800/57* (2013.01)

(58) Field of Classification Search
CPC .. A61K 8/11; A61K 2800/48; A61K 2800/57; A61K 8/8152; A61K 8/26; A61K 2800/56; A61K 8/731; A61Q 13/00
USPC ........................................................ 512/4, 1
See application file for complete search history.

(56) References Cited

U.S. PATENT DOCUMENTS

| 6,143,353 | A | * | 11/2000 | Oshlack | ............... | A61K 9/5078 |
| | | | | | | 427/2.14 |
| 6,454,842 | B1 | | 9/2002 | Vernardakis et al. | | |
| 8,921,303 | B1 | * | 12/2014 | Lull | ........................ | A61L 9/013 |
| | | | | | | 424/70.11 |
| 2003/0076393 | A1 | | 4/2003 | Lee | | |
| 2005/0137326 | A1 | | 6/2005 | Sanfilippo | | |
| 2005/0244349 | A1 | * | 11/2005 | Chaudhuri | ............... | A61K 8/37 |
| | | | | | | 424/59 |
| 2006/0287205 | A1 | | 12/2006 | Popplewell et al. | | |
| 2010/0310671 | A1 | * | 12/2010 | Malotky | .................. | A61K 8/11 |
| | | | | | | 424/501 |
| 2016/0287205 | A1 | * | 10/2016 | Zou | ........................ | A61B 6/585 |

FOREIGN PATENT DOCUMENTS

| DE | 1913569 A1 | 10/1969 |
| WO | 2005070371 A2 | 8/2005 |
| WO | 2008115961 A2 | 9/2008 |
| WO | 2009064739 A1 | 5/2009 |
| WO | 2014011860 A2 | 1/2014 |

OTHER PUBLICATIONS

International Search Report Application No. PCT/IL2015/050088 Completed: May 5, 2015; dated May 6, 2015 11 pages.

* cited by examiner

*Primary Examiner* — Jessica Whiteley
(74) *Attorney, Agent, or Firm* — The Roy Gross Law Firm, LLC; Roy Gross

(57) ABSTRACT

A fragrance releasing complex with extended fragrance retention capability including an acrylic polymer, to be applied a human body surface is provided. The fragrance releasing complex can be applied by using a kit which includes means for applying the fragrance releasing complex to the body surface.

18 Claims, No Drawings

SCENTED BODY COMPOSITIONS

BACKGROUND OF THE INVENTION

Since early human history, scents and fragrances have been used to modify body odor. They were obtained in raw form such as resins, gums or essential oils and derived from natural sources, such as the bark, roots, leaves and fruit of indigenous plants and trees. These raw materials were then diluted with water or other solvents and applied to the skin. In modern times, the chemical components responsible for the odor properties of these raw materials were isolated and identified. Current day perfumery engages in combining various fragrance materials to obtain novel fragrance compositions with specific "characteristics".

In light of the advancements in chemical technology many fragrances are no longer derived from natural sources but are synthesized as highly pure fragrance raw materials (FRM). Furthermore, fragrances have been categorized into three "note" types based on their relative volatility; base, having the most long lasting aroma; middle having a medium volatility, and top notes being the most volatile. If used correctly the different note combinations can produce a "balanced fragrance" composition i.e. one which diffuses in a manner having an aesthetic pleasing effect.

In addition, fragrances have been grouped according to the odor they produce, by using both broad and specific descriptions. For example, "floral" is a term used for odors associated with flowers while the term "lilac" is more specific. Additional examples of descriptive terms include "rose", "floral", "green", "citrus", "spicy", "honey", and "musk".

Due to an uneven evaporation rate of the different components, the initial fragrance may be quite different from the aroma perceived several hours later. Several methods have been commonly employed to address this issue. One method is to "load up" on the perfume initially and rely on the natural evaporation rate to diminish the fragrance so as to reach a suitable level several hours later when the desired effect is required. Another method is to continually reapply small amounts of the perfume to the skin at short time intervals. However neither of these solutions overcomes the problem of the diminishing level of top and middle notes over time. In fact, base notes which are present over an extended period in light of their low volatility, begin to accumulate with each renewed appliance of perfume, with the possible outcome of overwhelming the other fragrance notes and negating the original fragrance balance.

Acrylic acid (prop-2-enoic acid) is an organic compound with the formula $CH_2=CHCO_2H$. It consists of a vinyl group connected directly to a carboxylic acid terminus and is the simplest unsaturated carboxylic acid. It is a colorless liquid with an acrid or tart smell. It is miscible with water, alcohols, ethers, and chloroform. It is used extensively in different forms and more than one billion kilograms are produced annually. Acrylic acid is produced from propene which is a byproduct of ethylene and gasoline production.

Acrylate polymers belong to a group of polymers which are commonly referred to as plastics. Some of their notable characteristics include transparency, resistance to breakage, and elasticity. They are also generally known as acrylics or polyacrylates. Acrylate polymers are formed from Acrylate monomers which are based on the structure of acrylic acid or are derivatives of acrylic acid, such as methyl methacrylate in which one vinyl hydrogen and the carboxylic acid hydrogen are both replaced by methyl groups, and acrylonitrile in which the carboxylic acid group is replaced by the related nitrile group.

Acrylic paint is a paint containing a pigment suspension in an acrylic polymer emulsion. It can be diluted with water, but becomes water-resistant when dry. Depending on the degree to which the paint is diluted with water, or modified with acrylic gels, media, or pastes, the finished acrylic painting can have unique characteristics not attainable with other media.

SUMMARY OF THE INVENTION

In one embodiment, this invention provides a composition and/or a fragrance-releasing complex comprising: (1) a fragrance; and (2) a fragrance retention composition, the fragrance retention composition comprises an acrylic polymer wherein the fragrance-releasing complex is adapted to extend fragrance retention. In one embodiment, this invention provides a composition comprising: (1) a fragrance; and (2) an acrylic polymer. In one embodiment, this invention provides a composition comprising: (1) a fragrance; and (2) an acrylic polymer, wherein the fragrance is embedded within the acrylic polymer.

In a further embodiment, this invention provides a fragrance-releasing complex, comprising from 50 to 80% by weight polymer.

In a further embodiment, this invention provides a composition and/or a fragrance-releasing complex, wherein the acrylic polymer is within an emulsion. In a further embodiment, this invention provides a fragrance-releasing complex, wherein the emulsion is an acrylic paint.

In a further embodiment, this invention provides a composition and/or a fragrance-releasing complex, wherein the fragrance comprises: an alcohol, an ether, a nitrile, an aldehyde, an ester, a ketone, a lactone, a thiol, an amine, a schiff-base, a terpene, a cyclic alkene, a cyclic oxide, an oxime, an essential oil, an aromatic species, or any combination thereof.

In a further embodiment, this invention provides a composition and/or a fragrance-releasing complex, wherein the fragrance comprises: i) a base note fragrance; ii) a middle note fragrance; iii) a top note fragrance; iv) a balance carrier; v) a fixative, or any combination thereof.

In a further embodiment, this invention provides a composition and/or a fragrance-releasing complex, wherein the fragrance comprises a solvent suitable for human topical administration.

In a further embodiment, this invention provides a composition and/or a fragrance-releasing complex, wherein the fragrance comprises a volatile fragrance.

In a further embodiment, this invention provides a composition or a fragrance-releasing complex, retaining a perceptible fragrance for 15 to 40 hours.

In a further embodiment, this invention provides a method for conferring, enhancing, improving or modifying the odor properties of a body surface, comprising contacting or treating the body surface with the fragrance-releasing complex.

In a further embodiment, this invention provides a method for decorating the body surface.

In a further embodiment, this invention provides a kit for applying a fragrance to a subject, comprising the composition and/or fragrance-releasing complex and means for topically applying the fragrance-releasing complex to a body surface of a subject.

In a further embodiment, this invention provides a kit wherein applying a fragrance to a subject is further applying a body decoration.

In a further embodiment, this invention provides a kit wherein the composition and/or the fragrance-releasing complex comprise a pigment.

DETAILED DESCRIPTION OF THE INVENTION

In one embodiment, the present invention provides a composition comprising: a fragrance; an acrylic polymer, a thickener, an emulsifier, an aqueous solution, and a pigment. In another embodiment, the composition is a visible fragrance-releasing complex. In another embodiment, visible is visible light. In another embodiment, a composition of the invention is a scented body composition. In another embodiment, a composition of the invention is a topical scented body composition. In another embodiment, a composition of the invention is a topical scented colored body composition and/or decoration.

In another embodiment, an aqueous solution is water, distilled water, or purified water. In another embodiment, an aqueous solution is a buffer. In another embodiment, an aqueous solution is an isotonic buffer.

In another embodiment, an emulsifier is a nonionic emulsifier. In another embodiment, an emulsifier is any nonionic emulsifier known to one of average skill in the art. In another embodiment, an emulsifier is a combination of emulsifiers or a combination of nonionic emulsifiers.

In another embodiment, a composition as described herein is stable after it was applied to the skin or a body surface and is dried. In another embodiment, a stable composition is a composition no affected by cracks and/or peelings. In another embodiment, a stable composition is a composition which releases noticeable amount of fragrance for at least 8 hours. In another embodiment, a stable composition is a composition which releases a noticeable amount of fragrance for at least 10 hours. In another embodiment, a stable composition is a composition which releases a noticeable amount of fragrance for at least 12 hours. In another embodiment, a stable composition is a composition which releases a noticeable amount of fragrance for at least 15 hours. In another embodiment, a stable composition is a composition which releases a noticeable amount of fragrance for at least 20 hours. In another embodiment, a stable composition is a composition which releases a noticeable amount of fragrance for at least 24 hours. In another embodiment, a stable composition is a composition which releases a noticeable amount of fragrance for 8 to 36 hours.

In another embodiment, a stable composition is a composition which releases a noticeable amount of fragrance within 2 to 120 seconds from applying it to a skin surface (immediate fragrance release). In another embodiment, a stable composition is a composition which releases a noticeable amount of fragrance within 1 to 15 seconds from applying it to a skin surface (immediate fragrance release). In another embodiment, a stable composition is a composition which releases a noticeable amount of fragrance within 5 to 30 seconds from applying it to a skin surface (immediate fragrance release). In another embodiment, a stable composition is a composition which releases a noticeable amount of fragrance within 10 to 40 seconds from applying it to a skin surface (immediate fragrance release).

In another embodiment, an emulsifier is Glyceryl Stearate. In another embodiment, an emulsifier is a Polysorbate. In another embodiment, an emulsifier is Polysorbate 80. In another embodiment, an emulsifier is Polysorbate 20. In another embodiment, an emulsifier is Ceteareth-20.

In another embodiment, a thickener is a cosmetic thickener. In another embodiment, a thickener comprises cellulose or a derivative thereof. In another embodiment, a thickener is an aqueous thickener. In another embodiment, a thickener comprises clay. In another embodiment, a thickener comprises a gum. In another embodiment, a thickener comprises a carbomer. In another embodiment, a thickener comprises a polyethylene glycol. In another embodiment, a thickener comprises a non-aqueous thickener. In another embodiment, a thickener is an organic thickener. In another embodiment, a thickener is an organoclay.

In another embodiment, a thickener is a clay based thickener having a density of at least 1 $g/cm^3$. In another embodiment, a thickener is a clay based thickener having a density of 1 to 2.5 $g/cm^3$. In another embodiment, a thickener is a clay based thickener having a density of 1.2 to 2.0 $g/cm^3$. In another embodiment, a thickener is a clay based thickener having a density of 1 to 1.8 $g/cm^3$. In another embodiment, a thickener is a clay based thickener having a density of 1.4 to 2.0 $g/cm^3$. In another embodiment, a thickener is a clay based thickener having a density of about 1.6 $g/cm^3$.

In another embodiment, the invention provides a composition and/or a fragrance-releasing complex comprising: at least one fragrance and a fragrance retention composition. In one embodiment, this invention provides a composition comprising: (1) a fragrance; and (2) an acrylic polymer. In one embodiment, this invention provides a composition comprising: (1) a fragrance; and (2) an acrylic polymer, wherein the fragrance is embedded within the acrylic polymer. In one embodiment, the fragrance retention composition comprises an acrylic polymer. In another embodiment, the fragrance-releasing complex is adapted to extend fragrance retention within the acrylic polymer. In another embodiment, the acrylic polymer engulfs, encapsulates, and/or retains a fragrance. In another embodiment, the acrylic polymer provides a solid or a semi-solid vehicle to a fragment. In another embodiment, the acrylic polymer provides a gel, a semi-gel, or a viscous vehicle to a fragment. In another embodiment, the acrylic polymer is in the form of a pattern that adheres to a body surface. In another embodiment, the fragrance-releasing complex is non-irritable, non-allergenic, non-toxic or any combination thereof to a body surface such as skin. In another embodiment, the acrylic polymer has a pH value of 7 to 9. In another embodiment, the acrylic polymer has a pH value of 7.5 to 8.5.

In another embodiment, a composition as described herein forms a film once applied to a surface. In another embodiment, the quality of film correlates to the stability of the formulation on a surface. In another embodiment, the quality of film correlates to the stability of the formulation on the skin.

In one embodiment, the term "comprises" includes or can be replaced with the term "consists".

In one embodiment, the term "about", as used herein, means within 10% of the recited numerical value; In another embodiment, the term "about" as used herein, means within 5% of the recited numerical value.

In one embodiment, the term "fragrance-releasing complex" is synonymous with the term "composition" as used herein.

In another embodiment, a composition comprising: a fragrance; an acrylic polymer, a thickener, an emulsifier, an aqueous solution, and a pigment is used for skin or a body surface decoration. In another embodiment, a composition as described herein is a visible fragrance-releasing complex. In another embodiment, a composition as described herein is active for at least 10 hours. In another embodiment, a composition as described herein is active for at least 12 hours. In another embodiment, a composition as described herein is active for at least 15 hours. In another embodiment, a composition as described herein is active for at least 18 hours. In another embodiment, a composition as described herein is active for at least 20 hours. In another embodiment, a composition as described herein is active for 10 to 40 hours. In another embodiment, a composition as described herein is active for 10 to 30 hours. In another embodiment, a composition as described herein is active for 10 to 25 hours.

In another embodiment, active is visible upon placement on a body surface. In another embodiment, active is air exposed. In another embodiment, active is air exposed but not liquid exposed. In another embodiment, active is a noticeable amount of fragrance for at least 5 hours. In another embodiment, active is a noticeable amount of fragrance for at least 10 hours. In another embodiment, active is a noticeable amount of fragrance for at least 15 hours. In another embodiment, active is a noticeable amount of fragrance for at least 25 hours. In another embodiment, active is a noticeable amount of fragrance for 5 to 40 hours. In another embodiment, active is a noticeable amount of fragrance for 10 to 40 hours. In another embodiment, active is a noticeable amount of fragrance for 15 to 40 hours. In another embodiment, active is a noticeable amount of fragrance for 15 to 35 hours.

In another embodiment, noticeable scent or fragrance is when at least one healthy adult individual can detect or smell a fragrance from a composition placed at a distance of 5 cm from his or hers nose. In another embodiment, "noticeable" is smellable (capable of being smelled) amount of fragrance noticed by healthy and normal human nose of three adult female individuals from a distance of 5 cm from the composition as described herein. In another embodiment, unnoticeable scent or fragrance is when at least one healthy adult female individual of three adult female individuals cannot detect or smell a fragrance from a composition placed at a distance of 5 cm from her nose.

In another embodiment, the composition as described herein comprises a fragrance in an amount of from 2 to 40% by weight of the total composition. In another embodiment, the composition as described herein comprises a fragrance in an amount of from 5 to 30% by weight of the total composition. In another embodiment, the composition as described herein comprises a fragrance in an amount of from 5 to 20% by weight of the total composition. In another embodiment, the composition as described herein comprises a fragrance in an amount of from 5 to 15% by weight of the total composition. In another embodiment, the composition as described herein comprises a fragrance in an amount of from 7 to 15% by weight of the total composition.

In another embodiment, a recitation of weight percent as described herein is weight percent from/of the total composition.

In another embodiment, the composition as described herein comprises from 0.2 to 8% by weight thickener. In another embodiment, the composition as described herein comprises from 0.2 to 5% by weight thickener. In another embodiment, the composition as described herein comprises from 0.2 to 4% by weight thickener. In another embodiment, the composition as described herein comprises from 0.5 to 3% by weight thickener. In another embodiment, the composition as described herein comprises from 0.5 to 2.5% by weight thickener.

In another embodiment, the composition as described herein comprises from 0.2 to 8% by weight emulsifier. In another embodiment, the composition as described herein comprises from 0.2 to 5% by weight emulsifier. In another embodiment, the composition as described herein comprises from 0.2 to 4% by weight emulsifier. In another embodiment, the composition as described herein comprises from 0.5 to 3% by weight emulsifier. In another embodiment, the composition as described herein comprises from 0.5 to 2.5% by weight emulsifier.

In another embodiment, the composition as described herein comprises from 2 to 30% by weight aqueous solution. In another embodiment, the composition as described herein comprises from 5 to 15% by weight aqueous solution. In another embodiment, the composition as described herein comprises from 8 to 12% by weight aqueous solution. In another embodiment, the composition as described herein comprises from 8 to 25% by weight aqueous solution. In another embodiment, the composition as described herein comprises from 15 to 28% by weight aqueous solution. In another embodiment, the composition as described herein comprises from 10 to 30% by weight aqueous solution.

In another embodiment, the composition as described herein comprises from 2 to 50% by weight pigment. In another embodiment, the composition as described herein comprises from 5 to 30% by weight pigment. In another embodiment, the composition as described herein comprises from 5 to 20% by weight pigment. In another embodiment, the composition as described herein comprises from 15 to 30% by weight pigment. In another embodiment, the composition as described herein comprises from 7 to 15% by weight pigment. In another embodiment, the composition as described herein comprises from 25 to 40% by weight pigment. In another embodiment, the composition as described herein comprises from 25 to 35% by weight pigment.

In another embodiment, the composition as described herein comprises: from 30 to 75% by weight acrylic polymer, from 10 to 40% by weight pigment, from 0.4 to 4% by weight thickener, from 0.5 to 2.5% by weight emulsifier, from 8 to 42% by weight aqueous solution, and from 7 to 15% by weight fragrance.

In another embodiment, the composition as described herein comprises: from 40 to 80% by weight acrylic polymer, from 1 to 20% by weight pigment, from 0.1 to 2% by weight thickener, from 0.5 to 2.0% by weight emulsifier, from 3 to 20% by weight aqueous solution, and from 1 to 10% by weight fragrance.

In another embodiment, the composition as described herein solidifies, dries, and/or stabilizes within 5 to 50 seconds after exposure to air at a temperature of 15 to 30° C. In another embodiment, the composition as described herein solidifies, dries, and/or stabilizes within 5 to 50 seconds after it is applied on a body surface at an ambient temperature of 15 to 30° C. In another embodiment, the composition as described herein solidifies, dries, and/or stabilizes within 5 to 50 seconds after it is applied onto the skin at an ambient temperature of 15 to 30° C. In another embodiment, the composition as described herein solidifies, dries, and/or stabilizes within 5 to 50 seconds after it is applied onto a cloth at an ambient temperature of 15 to 30° C. In another embodiment, a stabilized composition is a composition that does not stain another surface upon contact with another surface. In another embodiment, a stabilized composition is a solid composition. In another embodiment, a stabilized composition is a composition that sticks to a body surface.

In another embodiment, the composition as described herein solidifies, dries, and/or stabilizes within 5 to 30 seconds. In another embodiment, the composition as described herein solidifies, dries, and/or stabilizes within 10 to 40 seconds. In another embodiment, the composition as described herein solidifies, dries, and/or stabilizes within 10 to 20 seconds. In another embodiment, the composition as described herein solidifies, dries, and/or stabilizes within 10 to 30 seconds.

In another embodiment, each physical measure described herein is obtained under standard conditions for temperature and pressure (STP) or STAP if not otherwise stated.

In another embodiment, a thickener of the invention has a density of 0.5 to 2.5 g/cm$^3$ at 20° C. In another embodiment, a thickener of the invention has a density of 0.7 to 2.2 g/cm$^3$ at 20° C. In another embodiment, a thickener of the invention has a density of 0.7 to 1.8 g/cm$^3$ at 20° C. In another embodiment, a thickener of the invention has a density of 0.9 to 1.6 g/cm$^3$ at 20° C.

In another embodiment, an acrylic polymer has a viscosity of 1500 to 12000 mPas. In another embodiment, an acrylic polymer has a viscosity of 2500 to 10000 mPas. In another embodiment, an acrylic polymer has a viscosity of 2500 to 7500 mPas. In another embodiment, an acrylic polymer has a viscosity of 2000 to 4000 mPas. In another embodiment, an acrylic polymer has a viscosity of 3000 to 6000 mPas.

In another embodiment, an acrylic polymer of the invention has a density of 0.5 to 2.5 g/cm$^3$ at 20° C. In another embodiment, an acrylic polymer of the invention has a density of 0.7 to 2.2 g/cm$^3$ at 20° C. In another embodiment, an acrylic polymer of the invention has a density of 0.7 to 1.8 g/cm$^3$ at 20° C. In another embodiment, an acrylic polymer of the invention has a density of 0.8 to 1.5 g/cm$^3$ at 20° C.

In another embodiment, an acrylic polymer has an ultimate tensile strength of 7 to 12 N/mm$^2$. In another embodiment, an acrylic polymer has an ultimate tensile strength of 8 to 12 N/mm$^2$. In another embodiment, an acrylic polymer has an ultimate tensile strength of 8 to 10 N/mm$^2$. In another embodiment, an acrylic polymer has an ultimate tensile strength of 8.5 to 9.5 N/mm$^2$.

In another embodiment, an acrylic polymer has an elongation at break measure of 200 to 800%. In another embodiment, an acrylic polymer has an elongation at break measure of 300 to 800%. In another embodiment, an acrylic polymer has an elongation at break measure of 300 to 700%. In another embodiment, an acrylic polymer has an elongation at break measure of 400 to 600%. In another embodiment, an acrylic polymer has an elongation at break measure of 450 to 550%.

In another embodiment, an acrylic polymer has an E-modulus of 0.5 to 5 N/mm$^2$. In another embodiment, an acrylic polymer has an E-modulus of 1 to 4 N/mm$^2$. In another embodiment, an acrylic polymer has an E-modulus of 1 to 3 N/mm$^2$. In another embodiment, an acrylic polymer has an E-modulus of 1.5 to 2.5 N/mm$^2$.

In another embodiment, an acrylic polymer of the invention comprises from 30 to 75% solid content. In another embodiment, an acrylic polymer of the invention comprises from 40 to 75% solid content. In another embodiment, an acrylic polymer of the invention comprises from 40 to 60% solid content. In another embodiment, an acrylic polymer of the invention comprises from 45 to 55% solid content.

In another embodiment, a pigment of the invention has a density of 1 to 10 g/cm$^3$ at 20° C. In another embodiment, a pigment of the invention has a density of 1.5 to 5 g/cm$^3$ at 20° C. In another embodiment, a pigment of the invention has a density of 1 to 3 g/cm$^3$ at 20° C. In another embodiment, a pigment of the invention has a density of 2 to 4 g/cm$^3$ at 20° C.

In another embodiment, a pigment of the invention comprises aluminum. In another embodiment, a pigment of the invention comprises titanium dioxide. In another embodiment, a pigment of the invention comprises silicon dioxide.

In one embodiment, the fragrance-releasing complex comprises a retention composition. In another embodiment, the fragrance-releasing complex comprises a combination of retention compositions. In one embodiment, the fragrance-releasing complex comprises a fragrance. In another embodiment, the fragrance-releasing complex comprises a combination of fragrances. In another embodiment, the present invention provides a composition and/or a fragrance-releasing complex comprising one or more fragrances and one or more fragrance retention compositions. In another embodiment, the fragrance-releasing complex comprises an admixture or an accord.

In another embodiment, the fragrance retention composition comprises an acrylic polymer or a combination of acrylic polymers. In another embodiment, the acrylic polymer, is comprises starch or modified starch. In another embodiment, the acrylic polymer, is a: homopolymer, copolymer or multipolymer of one or more monomers including, but not limited to, acrylic acid, methacrylic acid, esters of acrylic acid and methacrylic acid (acrylates and methacrylates), acrylamides, acrylonitriles and derivatives and any combinations thereof. In another embodiment, the acrylic polymer comprises acrylate monomers, such as but not limited to: Methacrylate, Methyl acrylate, Ethyl acrylate, 2-Chloroethyl vinyl ether, 2-Ethylhexyl acrylate, Hydroxyethyl methacrylate, Butyl acrylate, Butyl methacrylate, trimethylolpropane triacrylate (TMPTA) and any combination thereof. In another embodiment, the acrylic polymer is a copolymer-dispersion of acrylic and methacrylic acid esters.

In another embodiment, an acrylic polymer is an acrylate polymer or copolymer. In another embodiment, the fragrance retention composition comprises solid polymers such as PMMA (polymethyl methacrylate). In another embodiment, the fragrance retention composition comprises silica. In another embodiment, the fragrance retention composition comprises methyl methacrylate. In another embodiment, the fragrance retention composition comprises acrylated beads. In another embodiment, the fragrance retention composition comprises microparticles comprising polymers of the invention. In another embodiment, the fragrance retention composition comprises nanoparticles comprising polymers of the invention. In another embodiment, the acrylic polymer is a copolymer. In another embodiment, the acrylic polymer is a dispersion of acrylic and methacrylic acid esters.

In another embodiment, the fragrance retention composition is nonporous. In another embodiment, the fragrance retention composition comprises a composite product such as but not limited to: PMMA 2MUSI. In another embodiment, the fragrance retention composition is a film-forming agent. In another embodiment, the fragrance retention composition comprises a wax, a resin, a gum, cellulose, polyquaternium and any combination thereof. In another embodiment, the fragrance retention composition comprises any cosmetic polymer and/or copolymer.

In one embodiment, the fragrance retention composition has the capacity to affect the characteristics of the fragrance composition, such as but not limited to, limiting evaporation rate and intensity, in a manner that can be perceived by an observer or user thereof, over time, as compared to the same perception in the absence of the fragrance retention composition. In another embodiment, the fragrance retention composition is non-irritable, non-allergenic, non-toxic or any combination thereof to a body surface such as skin. In another embodiment, the fragrance retention composition thickens upon exposure to air. In another embodiment, the fragrance retention composition dries upon exposure to air. In another embodiment, the fragrance retention composition solidifies upon exposure to air.

In one embodiment, the present invention provides a fragrance-releasing complex, wherein the weight ratio of the fragrance to the acrylic polymer is at least 1:90. In another embodiment, the weight ratio of the fragrance to the acrylic polymer is about 1:50. In another embodiment, the weight ratio of the fragrance to the acrylic polymer is about 1:30. In another embodiment, the weight ratio of the fragrance to the acrylic polymer is from about 1:175 to 1:3. In another embodiment, the weight ratio of the fragrance to the acrylic polymer is from about 1:150 to 1:3. In another embodiment, the weight ratio of the fragrance to the acrylic polymer is from about 1:150 to 1:4. In another embodiment, the weight ratio of the fragrance to the acrylic polymer is from about 1:135 to 1:4. In another embodiment, the weight ratio of the fragrance to the acrylic polymer is from about 1:135 to 1:30. In another embodiment, the weight ratio of the fragrance to the acrylic polymer is from about 1:200 to 1:10. In another embodiment, the weight ratio of the fragrance to the acrylic polymer is from about 1:120 to 1:30. In another embodiment, the weight ratio of the fragrance to the acrylic polymer is from about 1:500 to 1:100. In another embodiment, the weight ratio of the fragrance to the acrylic polymer is from about 1:100 to 1:10. In another embodiment, the weight ratio of the fragrance to the acrylic polymer is from about 1:90 to 1:15. In another embodiment, the weight ratio of the fragrance to the acrylic polymer is from about 1:90 to 1:10. In another embodiment, the weight ratio of the fragrance to the acrylic polymer is from about 1:75 to 1:8. In another embodiment, the weight ratio of the fragrance to the acrylic polymer is from about 1:75 to 1:9. In another embodiment, the weight ratio of the fragrance to the acrylic polymer is from about 1:60 to 1:9. In another embodiment, the weight ratio of the fragrance to the acrylic polymer is from about 1:60 to 1:10. In another embodiment, the weight ratio of the fragrance to the acrylic polymer is from about 1:45 to 1:10. In another embodiment, the weight ratio of the fragrance to the acrylic polymer is from about 1:45 to 1:15.

In one embodiment, the acrylic polymer is within an emulsion. In another embodiment, an emulsion is oil in water emulsion. In another embodiment, an emulsion is water in oil emulsion. In another embodiment, the acrylic polymer is within dispersion. In another embodiment, the acrylic polymer is within a suspension.

In one embodiment, the emulsion comprises polyethyl acrylate, polymethyl acrylate, a copolymer of ethyl acrylate, and/or methyl methacrylate. In one embodiment, the emulsion comprises an ethylenically unsaturated compound such as, but not limited to: styrene. In another embodiment, the emulsion comprises a higher alkyl methacrylate.

In one embodiment, the emulsion is an acrylic paint. In one embodiment, the term "acrylic paint" refers to water based paint. In another embodiment the term acrylic paint refers to latex paint. In another embodiment the term acrylic paint refers to emulsion paint. In another embodiment the term acrylic paint refers to water soluble paint.

In one embodiment, the fragrance retention composition comprises a pigment. In another embodiment, the fragrance retention composition comprises a dispersing agent. In another embodiment, the fragrance retention composition comprises a solubilization accelerating agent. In another embodiment, the fragrance retention composition comprises an inorganic filler. In another embodiment, the fragrance retention composition comprises a binding agent. In another embodiment, the fragrance retention composition comprises a resin. In another embodiment, the fragrance retention composition comprises a rheological agent. In another embodiment, the fragrance retention composition comprises an anti-foaming agent.

In one embodiment, the pigment is an organic pigment. In another embodiment, the pigment is an inorganic pigment. In one embodiment, the pigment is a combination of pigments. In one embodiment, the pigment is a combination of inorganic and organic pigments. In another embodiment, the pigment is a colorant. In another embodiment, the pigment comprises a combination of colorants. In another embodiment, the pigment is a dye. In another embodiment, the pigment comprises a combination of dyes. In one embodiment, the pigment comprises a colored component. In another embodiment, the pigment comprises a combination of colored components. In another embodiment, the pigment is an ink. In another embodiment, the pigment comprises a combination of inks.

In another embodiment, the pigment comprises: an anthraquinone, a phthalocyanine, a pyrroline, a triphenodioxazine, a methine, a benzodifuranone, a coumarin, an indoaniline, a benzenoid, a xanthene, a phenazine, a solvent soluble sulphur dye, a quinophthalone, a pyridone, an aminopyrazoie, a pyrollidine, a styrylic and any combination thereof. In another embodiment, the pigment comprises an azoic, such as, but not limited to, a monoazo, a disazo, a trisazo and any combination thereof. In another embodiment, the pigment comprises an azoic containing a heterocyclic group.

In one embodiment, the fragrance retention composition comprises, about 30% to 95% by weight of a pigment. In one embodiment, the fragrance retention composition comprises, about 30% to 90% by weight of a pigment. In one embodiment, the fragrance retention composition comprises, about 40% to 90% by weight of a pigment. In one embodiment, the fragrance retention composition comprises, about 40% to 80% by weight of a pigment. In one embodiment, the fragrance retention composition comprises, about 50% to 80% by weight of a pigment. In one embodiment, the fragrance retention composition comprises, about 50% to 70% by weight of a pigment. In one embodiment, the fragrance retention composition comprises, about 60% to 70% by weight of a pigment.

In one embodiment, the fragrance retention composition comprises, about 0.5% to 30% by weight of a dispersing agent. In one embodiment, the fragrance retention composition comprises, about 0.5% to 25% by weight of a dispersing agent. In one embodiment, the fragrance retention composition comprises, about 1.5% to 25% by weight of a dispersing agent. In one embodiment, the fragrance retention composition comprises, about 3% to 20% by weight of a dispersing agent. In one embodiment, the fragrance retention composition comprises, about 5% to 20% by weight of a dispersing agent. In one embodiment, the fragrance retention composition comprises, about 5% to 10% by weight of a dispersing agent.

In another embodiment, the fragrance retention composition comprises, about 2% to 50% by weight of a solubilization accelerating agent. In another embodiment, the fragrance retention composition comprises, about 2% to 40% by weight of a solubilization accelerating agent. In another embodiment, the fragrance retention composition comprises, about 5% to 40% by weight of a solubilization accelerating agent. In another embodiment, the fragrance retention composition comprises, about 5% to 35% by weight of a solubilization accelerating agent. In another embodiment, the fragrance retention composition comprises, about 5% to 30% by weight of a solubilization accelerating agent. In another embodiment, the fragrance retention composition comprises, about 10% to 20% by weight of a solubilization accelerating agent. In another embodiment, the fragrance retention composition comprises, about 15% to 20% by weight of a solubilization accelerating agent.

In another embodiment, the fragrance retention composition comprises, about 1% to 50% by weight of inorganic filler. In another embodiment, the fragrance retention composition comprises, about 1% to 40% by weight of inorganic filler. In another embodiment, the fragrance retention composition comprises, about 3% to 40% by weight of inorganic filler. In another embodiment, the fragrance retention composition comprises, about 5% to 40% by weight of inorganic filler. In another embodiment, the fragrance retention composition comprises, about 5% to 35% by weight of inorganic filler. In another embodiment, the fragrance retention composition comprises, about 5% to 30% by weight of inorganic filler. In another embodiment, the fragrance retention composition comprises, about 10% to 20% by weight of inorganic filler. In another embodiment, the fragrance retention composition comprises, about 15% to 20% by weight of inorganic filler.

In another embodiment, the fragrance retention composition comprises, about 1 to 10% by weight of a binding agent. In another embodiment, the fragrance retention composition comprises, about 1 to 8% by weight of a binding agent. In another embodiment, the fragrance retention composition comprises, about 3 to 8% by weight of a binding agent. In another embodiment, the fragrance retention composition comprises, about 2 to 6% by weight of a binding agent. In another embodiment, the fragrance retention composition comprises, about 4 to 6% by weight of a binding agent.

In another embodiment, the fragrance retention composition comprises, about 1% to 50% by weight of a resin. In another embodiment, the fragrance retention composition comprises, about 1% to 40% by weight of a resin. In another embodiment, the fragrance retention composition comprises, about 3% to 40% by weight of a resin. In another embodiment, the fragrance retention composition comprises, about 5% to 40% by weight of a resin. In another embodiment, the fragrance retention composition comprises, about 5% to 35% by weight of a resin. In another embodiment, the fragrance retention composition comprises, about 5% to 30% by weight of a resin. In another embodiment, the fragrance retention composition comprises, about 10% to 20% by weight of a resin. In another embodiment, the fragrance retention composition comprises, about 15% to 20% by weight of a resin.

In one embodiment, the fragrance retention composition comprises, about 0.5% to 20% by weight of a rheological agent. In one embodiment, the fragrance retention composition comprises, about 0.5% to 17% by weight of a rheological agent. In one embodiment, the fragrance retention composition comprises, about 1.5% to 17% by weight of a rheological agent. In one embodiment, the fragrance retention composition comprises, about 1.5% to 15% by weight of a rheological agent. In one embodiment, the fragrance retention composition comprises, about 3% to 15% by weight of a rheological agent. In one embodiment, the fragrance retention composition comprises, about 3% to 10% by weight of a rheological agent. In one embodiment, the fragrance retention composition comprises, about 5% to 10% by weight of a rheological agent. In one embodiment, the fragrance retention composition comprises, about 5% to 7% by weight of a rheological agent.

In another embodiment, the fragrance retention composition comprises, about 0.5 to 10% by weight of an anti-foaming agent. In another embodiment, the fragrance retention composition comprises, about 0.5 to 8% by weight of an anti-foaming agent. In another embodiment, the fragrance retention composition comprises, about 1.5 to 8% by weight of an anti-foaming agent. In another embodiment, the fragrance retention composition comprises, about 1.5 to 6% by weight of an anti-foaming agent. In another embodiment, the fragrance retention composition comprises, about 3 to 6% by weight of an anti-foaming agent. In another embodiment, the fragrance retention composition comprises, about 3 to 4.5% by weight of an anti-foaming agent.

In one embodiment, the fragrance comprises: an alcohol, an ether, a nitrile, an aldehyde, an ester, a ketone, a lactone, a thiol, an amine, a schiff-base, a terpene, a cyclic alkene, a cyclic oxide, an oxime, an essential oil, an aromatic species, or any combination thereof.

In another embodiment the fragrance comprises a natural product, such as, but not limited to, an absolute, a resinoid, a resin and a concrete and any combination thereof.

In another embodiment the fragrance comprises a saturated compound, an unsaturated compound, an aliphatic compound, a carbocyclic compound and a heterocyclic compound and any combination thereof.

In another embodiment the fragrance comprises a component that is selected from the following: alicyclic ester, aliphatic ester, cyclic ester, aromatic ester, alicyclic ether, cyclic ether, aromatic ether, primary alcohols, tertiary alcohols, aromatic alcohols, cyclic alcohols, aliphatic aldehyde, cyclic aldehydes, aliphatic primary aldehyde, aromatic aldehydes, tertiary aldehydes, aliphatic ketones, aromatic ketones, cyclic ketones, macrocyclic ketones, aliphatic nitrile, aromatic nitrile, cyclic nitrile, 1,2-benzopyrone, Methyl 2-((-1-(2,4-dimethyl-3-cyclohexenyl)methylidene) amino)-1-benzenecarboxylate, Methyl 2-((-2-methylpentylidene)amino)-1-benzenecarboxylate, dimethyl-2-Methylene bicyclo (3,1,1) Heptane (6,6-), para-mentha-1,4(8)-diene, and any combination thereof.

In another embodiment the fragrance comprises a component that is selected from the following: an ethyl 2,6,6-trimethyl-1,3-cyclohexdiene-1-carboxylate, cis-beta-gamma-hexenyl acetate, 2-methylbuten-2-ol-4-acetate; glycolic acid, 2-pentyloxy:allyl ester, methyl-2-nonenoate, cis-beta-gamma-Hexenyl salicylate, 4-methyl-pentan-2-ol 2-butenoate, hexyl 2-butenoate, acetyl diisoamylene, 3-methylene-7-methyl-1-octen-7-yl acetate, methyl 2-nonenoate, citronellyl acetate, isobutyl angelate, tricyclo decenyl acetate, tricyclo decenyl propionate, 7-Acetyl, 1,2,3,4, 5,6,7,8-octahydro-1,1,6,7-tetramethyl naphtalene, givescone, allyl cyclohexyloxy acetate, 4(3)-(4-Methyl-3-pentenyl)-3-cyclohexenyl-methyl acetate, 2-cyclopentyl-cyclopentyl 2-butenoate, datilat, 6-Butyl-3,6-dihydro-2,4-dimethyl-2-hydro-pyran, 3,6-dihydro-4,6-dimethyl-2-phenyl-2hydro-pyran, 9-(Methyloxy)tricydo[5,2,1,0$^{2,6}$]dec-3-ene, beta gamma hexenol, 3,7-dimethyl-6-octen-1-ol, cis-3-hexenol, 9-Decen-1-ol, geraniol, 2,6-dimethyl-7-octen-2-ol, linalool, dihydro myrcenol, 3,7-Dimethyl-1,6-octadien-3-ol, 4-Methyl-3-decen-5-ol, amyl vinyl carbinol, 3-Phenyl-2-propen-1-ol, 2-Methyl-4-phenyl-1-pentanol, 2-Ethyl-4-(2,2,3-trimethyl-3-cyclopenten-1-yl)-2-buten-1-ol, 4,7-Methano-1H-inden-5-ol, 3a,4,5,6,7,7a-Hexahydro-2(or 3), 4-dimethyl, dimethyl cyclohexene methanol, 5(2,2,3-Trimethyl-3-cyclopentenyl)-3-methylpentan-2-ol, 1-Para-Menthen-4-ol, terpineol, ambrinol L20, 3,7-Dimethyl-6-octen-1-al, 2-Methl-4(2,6,6-trimethyl-1-cyclohexenyl-)2-butenal, 1-Methyl-4-(4-methylpentyl)-3-cyclohexenecarbaldehyde, 2,7-Dimethyloct-5-en-4-one 50% in Iso Propyl Myristate, Hexahydro Tetramethyl Methanonaphtalenone, 4-Penten-1-one, 1-(5,5-dimethyl-1-cyclohexen-1-yl)-, 5,8-Methano-2H-1-benzopyran; 6-ethylideneoctahydro-, 2-Buten-1-one; 1-(2,6,6-trimethyl-2-cyclohexen-1-yl)-, Diethyl dimethylcyclohex-2-en-1-one, 2-Buten-1-one, 1-(2,6,6-trimethyl-1-cyclohexen-1-yl)-, 2,5,10-Trimethyl-2,5,9-cyclododecatrien-1-yl methyl ketone, Methyl cedr-8-enyl ketone, Oxacyclohexadecen-2-one, 3,7-dimethyl-2,6-octadienenitrile, 3,12-tridecadiene nitrile, iris nitrile, ozonil, teamonyl, 5-Phenyl-3-methyl-penten-2-acid-nitrile, 2-Benzyl-2-methyl-3-butenenitril, rose nitrile, 1,2-benzopyrone, Methyl 2-((-1-(2,4-dimethyl-3-cyclohexenyl)methylidene) amino)-1-benzenecarboxylate, Methyl 2-((-2-methylpentyl-idene)amino)-1-benzenecarboxylate, Dimethyl-2-Methylene Bicyclo(3,1,1) Heptane (6,6-); Para-Mentha-1,4(8)-diene and any combination thereof.

In one embodiment, the fragrance comprises a base note fragrance. In one embodiment, the fragrance comprises a middle note fragrance. In one embodiment, the fragrance comprises a top note fragrance. In one embodiment, the fragrance comprises a balance carrier. In one embodiment, the term "balance carrier" is synonymous with the term "carrier" as used herein. In one embodiment, the fragrance comprises a carrier. In one embodiment, the fragrance comprises a fixative. In one embodiment, the term "fragrance" is synonymous with perfume. In another embodiment, the term "fragrance" means scent. In another embodiment, the term "fragrance" means aroma. In one embodiment, the term "fragrance", includes but is not limited to, conventional fragrances known in the art, including but not limited to, U.S. Pat. No. 4,145,184, Brain and Cummins, issued Mar. 20, 1979; U.S. Pat. No. 4,209,417, Whyte, issued Jun. 24, 1980; U.S. Pat. No. 4,515,705, Moeddel, issued May 7, 1985; and U.S. Pat. No. 4,152,272, Young, issued May 1, 1979, all of the patents being incorporated herein by reference.

In one embodiment, the top note fragrance, the middle note fragrance and the base note fragrance are scents that can be sensed with respect to the time after the application of a perfume.

In one embodiment, the top note fragrance has an evaporation coefficient (perfume notes) in the range of about 1 to 14. In one embodiment, the middle note fragrance has an evaporation coefficient (perfume notes) in the range of about 15 to 60. In one embodiment, the base note fragrance has an evaporation coefficient (perfume notes) in the range of about 61 to 100.

In one embodiment, the carrier comprises a component selected from the following: water, C1-C4 monohydric alcohol, C2-C6 polyhydric alcohol, propylene carbonate, liquid polyalkylene glycol and any combinations thereof.

In one embodiment, the fixative comprises a component selected from the following: Ambergris, sandalwood, musk, vetiver, orris root, and bergamot orange and any combinations thereof.

In one embodiment, the fragrance is selected according to the fragrance odor characteristics and other fragrance characteristics such as, but not limited to: viscosity, specific gravity, refractive index, saponification value and flash point or any combination thereof. In another embodiment the fragrance is selected according to fragrance odor characteristics obtained when combined with other components. In one embodiment, fragrance odor characteristics include a pleasant odor and/or clean odor such as, but not limited to: lavender, violet, rose, jasmin, pine, woody, floral, fruity, lemon, lime, apple, peach, raspberry, strawberry, banana, plum, apricot, vanilla, pear, eucalyptus, aromatic, aldehydic, tutti frutti, oriental, sweet, amber, Paola, Muguet, Citron (lime) ella and any combination thereof. In another embodiment the fragrance is selected according to fragrance characteristics obtained when combined with other components.

In another embodiment, fragrance odor characteristics and other fragrance characteristics include, but are not limited to, those given in "Perfume and Flavor Chemicals (Aroma Chemicals)," Steffen Arctander, published by the author, 1969. incorporated herein by reference.

In another embodiment the fragrance comprises a component that is selected from the following: anethole, benzaldehyde, decyl aldehyde, benzyl acetate, benzyl alcohol, benzyl formate, benzyl propionate, iso-bornyl acetate, camphene, cis-citral (neral), citronellal, citronellol, citronellyl acetate, paracymene, decanal, dihydrolinalool, dihydromyrcenol, methyl benzyl carbinyl acetate, dimethyl benzyl carbinyl acetate, dimethyl phenyl carbinol, eucalyptol, helional, geranial, geraniol, geranyl acetate, geranyl nitrile, cis-3-hexenyl acetate, dihydrocitronellal, d-limonene, linalool, linalool oxide, tetra-hydro linalool, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, phenyl acetaldehyde, alpha-pinene, beta-pinene, gamma-terpinene, terpineol, alpha-terpineol, beta-terpineol, terpinyl acetate, vertenex (para-tertiarybutyl cyclohexyl acetate), gamma-methyl ionone, undecalactone, undecylenic aldehyde, alpha-damascone, beta-damascone, amyl acetate, lemon oil, orange oil and any combination thereof.

In another embodiment the fragrance comprises a component that is selected from the following: hexyl cinnamic aldehyde, alpha-amylcinnamic aldehyde, p-anis aldehyde, cinnamic aldehyde, cuminic aldehyde, p-t-butyl-alpha-methyldihydrocinnamaldehyde, 4-hydroxy-3-methoxycinnamaldehyde, 2-phenyl-3-(2-furyl)prop-2-enal, vanillin isobutyrate, ethyl vanillin acetate, vanillin acetate, cyclamen aldehyde, heptanal, lauryl aldehyde, nonanal, octanal, phenyl propyl aldehyde, vanillin, salycil aldehyde, cytral, 2,4-dihydroxy-3-methylbenzaldehyde, 2-hydroxy-4-methylbenzaldehyde, 5-methyl salicylic aldehydes, 4-nitrobenzaldehyde, o-nitrobenzaldehyde, 5-ethyl-2-thiophenecarbaldehyde, 5-methyl-2-thiophenecarboxaldehyde, 2-thiophenecarb aldehyde, as aronaldehyde, 5-(hydroxymethyl)-2-furaldehyde, 2-benzofurancarboxaldehyde, 2-benzofurancarboxaldehyde, 4-ethoxy-3-methoxybenz aldehyde, Protocatechualdehyde, Heliotropine, 2,3,4-trimethoxybenz aldehyde, 3,4,5-trimethoxybenzaldehyde, 2,8-dithianon-4-3 n-4-carboxaldehyde. Sorbinaldehyde, 2,4-heptadienal, 2,4-decadienal, 2,4-nonadienal, (E,E)-,2,4-octadien-1-al, 2,4-octadienal, 2,4-dodec adienal, 4-undecadienal, 2,4-tridec adien-1-al, 2-trans-4-cis-7-cis-tridecatrienal, piperonylidene propionaldehyde, 2-methyl-3-(2-furyl)acrolein, 2,4-pentadienal, 2-furfurylidene butyraldehyde, 3-(2-furyl)acrolein, Pyruvaldehyde, Ethanedial, menthol, 3-buten-2-one, 3-methyl-4-(2,6,6-trimethyl-2-cyclohexen-1-yl), 4-(2,6,6-trimethylcyclohen-1-en-1-yl)but-3-en-2-one, 3-buten-2-one, 4-(2,6,6-trimethyl-2-cyclohexen-1-yl)-, (E)-, menthyl lactate, isomenthyl acetate, isomenthyl propionate, isomenthyl isobutyrate, camphor, p-menthane, cresol, tetra hydromyrcenol, cytronellol, cytronellyil derivatives, geranyl derivatives, linalyl acetate, mugetanol, eugenol, jasmal, pinanol, cedrene, beta pinene, cineole, nonadienol, ethylhexanal, octanol acetate, methyl furfural, terpinene, thujene, amylacetate, benzylacetate, di-hydrocumarin, 5 di-hydromyrcenyl acetate, Isoamylacetate, para-cymene, triethyl acetate, para-cresol, ethyl acetate, benzyl-benzoate, isopropyl myristate, methyl abietate, Ethanol, Isopropanol, diethyl sebacate, Glycerol, propylene glycol, 1,2-butylene glycol, dipropylene glycol, 2-methyl-2,4-pentanediol, diethylene glycol monoethyl ether, diethyl phthalate, hexyl salycilate, triethyl citrate, benzyl salicylate and any combination thereof. In another embodiment, the fragrance comprises the odor characteristics of the acrylic polymer.

In another embodiment, the fragrance includes, but is not limited to those disclosed in "Perfume and Flavor Chemicals (Aroma Chemicals)," Steffen Arctander, published by the author, 1969. incorporated herein by reference.

In one embodiment, the fragrance releasing complex comprises a solvent suitable for human topical administration. In another embodiment the solvent comprises a component selected from the following: dipropyleneglycol, diethyl phthalate, isopropyl myristate, benzyl benzoate, 2-(2-ethoxyethoxy)-1-ethanol or ethyl citrate, propylene glycol, triacetin, triethyl citrate, benzyl alcohol, ethanol, vegetable oil, terpene and any combination thereof.

In one embodiment, the fragrance releasing complex comprises a volatile fragrance.

In one embodiment, a volatile fragrance has a boiling point of less than about 475° C. to 525° C. In another embodiment a volatile fragrance has a boiling point of less than about 475° C. to 515° C. In another embodiment a volatile fragrance has a boiling point of less than about 485° C. to 515° C. In another embodiment a volatile fragrance has a boiling point of less than about 495° C. to 505° C. In another embodiment a volatile fragrance has a boiling point of less than about 500° C.

In one embodiment, a volatile fragrance is a highly volatile fragrance. In one embodiment, highly volatile fragrance means having a boiling point of about 230° C. to 250° C. or lower. In another embodiment highly volatile fragrance means having a boiling point of about 230° C. to 245° C. or lower. In another embodiment highly volatile fragrance means having a boiling point of about 235° C. to 245° C. or lower. In another embodiment highly volatile fragrance means having a boiling point of about 250° C. or lower.

In another embodiment the highly volatile fragrance comprises a component selected from the following: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol. geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevomenthyl acetate, menthone, iso-menthone. myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiarybutyl cyclohexyl acetate) and any combination thereof.

In one embodiment, a volatile fragrance is a moderately volatile fragrance. In one embodiment, a moderately volatile fragrance means having a boiling point of about 250° C. to 300° C. In another embodiment a moderately volatile fragrance means having a boiling point of about 250° C. to 300° C. In another embodiment a moderately volatile fragrance means having a boiling point of about 250° C. to 290° C. In another embodiment a moderately volatile fragrance means having a boiling point of about 260° C. to 290° C. In another embodiment a moderately volatile fragrance means having a boiling point of about 260° C. to 280° C.

In another embodiment, the moderately volatile fragrance comprises a component selected from the following: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, for acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, veratraldehyde and any combination thereof.

In one embodiment, a volatile fragrance is a less volatile fragrance. In one embodiment, a less volatile fragrance means having a boiling point of about 300° C. to 500° C. In another embodiment a less volatile fragrance means having a boiling point of about 300° C. to 450° C. In another embodiment a less volatile fragrance means having a boiling point of about 350° C. to 450° C.

In another embodiment, the less volatile fragrance comprises a component selected from the following: benzophenone, benzyl salicylate, ethylene brassyiate, galaxolide (1,3,4,6,7,8-hexahydro-4,6,6,7,8,8-hexamethyl-cyclopenta-gama-2-benzopyran), hexyl cinnamic aldehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, phenylethyl phenyl acetate and any combination thereof.

In one embodiment, the volatile fragrance is encapsulated or entrapped within the acrylic polymer. In one embodiment, the volatile fragrance is partially encapsulated within the acrylic polymer. In another embodiment the volatile fragrance is fully encapsulated within the acrylic polymer. In one embodiment, the volatile fragrance is partially entrapped within the acrylic polymer. In another embodiment the volatile fragrance is fully entrapped within the acrylic polymer.

In another embodiment, "retains a perceptible fragrance" is retains a perceptible fragrance after applied to a body surface. In another embodiment, "retains a perceptible fragrance" is smellable or detected by smell from a distance of 5 cm as described herein. In one embodiment, the fragrance-releasing complex retains a perceptible fragrance for at least 7 days. In another embodiment, the fragrance-releasing complex retains a perceptible fragrance attributable to the composition and/or the fragrance-releasing complex for 24 hours to 18 days. In another embodiment, the composition and/or the fragrance-releasing complex retains a perceptible fragrance attributable to the composition and/or the fragrance-releasing complex for 24 hours to 16 days. In another embodiment, the composition and/or the fragrance-releasing complex retains a perceptible fragrance attributable to the composition and/or the fragrance-releasing complex for 3 to 16 days. In another embodiment, the composition and/or the fragrance-releasing complex retains a perceptible fragrance attributable to the composition and/or the fragrance-releasing complex for 3 to 14 days. In another embodiment, the composition and/or the fragrance-releasing complex retains a perceptible fragrance attributable to the composition and/ or the fragrance-releasing complex for 5 to 14 days. In another embodiment, the composition and/or the fragrance-releasing complex retains a perceptible fragrance attributable to the composition and/or the fragrance-releasing complex for 5 to 12 days. In another embodiment, the composition and/or the fragrance-releasing complex retains a perceptible fragrance attributable to the composition and/ or the fragrance-releasing complex for 7 to 10 days. In another embodiment, the composition and/or the fragrance-releasing complex retains a perceptible fragrance attributable to the composition and/or the fragrance-releasing complex for 7 days. In another embodiment, the composition and/or the fragrance-releasing complex retains a perceptible fragrance attributable to the composition and/or the fragrance-releasing complex for 10 days.

In another embodiment, the composition and/or the fragrance-releasing complex retains a perceptible fragrance attributable to the composition and/or the fragrance-releasing complex for 10 to 50 hours. In another embodiment, the composition and/or the fragrance-releasing complex retains a perceptible fragrance attributable to the composition and/ or the fragrance-releasing complex for 10 to 40 hours. In another embodiment, the composition and/or the fragrance-releasing complex retains a perceptible fragrance attributable to the composition and/or the fragrance-releasing complex for 15 to 50 hours. In another embodiment, the composition and/or the fragrance-releasing complex retains a perceptible fragrance attributable to the composition and/ or the fragrance-releasing complex for 10 to 30 hours. In another embodiment, the composition and/or the fragrance-releasing complex retains a perceptible fragrance attributable to the composition and/or the fragrance-releasing complex for 15 to 30 hours. In another embodiment, the composition and/or the fragrance-releasing complex retains a perceptible fragrance attributable to the composition and/ or the fragrance-releasing complex for 18 to 28 hours. In another embodiment, the composition and/or the fragrance-releasing complex retains a perceptible fragrance attributable to the composition and/or the fragrance-releasing complex for 20 to 30 hours.

In one embodiment, the present invention provides a method for conferring, enhancing, improving or modifying the odor properties of a body surface, contacting or treating the body surface with the composition and/or the fragrance-releasing complex as described herein.

In one embodiment, the composition comprises an alcohol such as ethanol. In another embodiment the composition comprises a perfume concentrate. In another embodiment the composition comprises an eaux de parfum. In another embodiment, the composition comprises an eaux de toilette. In another embodiment the composition comprises a cologne. In another embodiment, the composition comprises a body splash.

In one embodiment, a fragrance means, a compound of current use in perfumery, which is used essentially for its ability to smell pleasantly and to be capable of imparting a pleasant odor to the products into which it is incorporated, or to the surfaces, such as, but not limited to, skin or hair, to which it is applied, on its own or in admixture with other components.

In another embodiment a fragrance is a composition capable to impart or modify the odor of a surface such as a body surface.

In another embodiment a fragrance is a composition that has the ability to mask a malodor of a surface.

In one embodiment, the present invention provides a method for decorating a body surface. In another embodiment, the body surface is skin. In one embodiment, the present invention provides a kit for applying a fragrance to a subject, comprising a fragrance-releasing complex; and means for topically applying the composition and/or the fragrance-releasing complex to a body surface of a subject.

In one embodiment, the kit comprises a stencil having a decorative shape therein. In another embodiment, the kit comprises a transferable sheet with a decorative shape thereon. In another embodiment, the kit comprises a cutout in the shape of the body decoration. In another embodiment, the kit comprises an image or pattern to be placed on any part of the human body.

In another embodiment, the kit comprises decorative element comprising a substrate, a decorative pattern thereon. In another embodiment, the substrate comprises a plastic film. In another embodiment, the plastic film comprises a polymer selected from the following: polyethylene, polypropylene, polyester, polyvinyl chloride and plasticized polyvinyl chloride; a metalized plastic film; and a metal foil.

In another embodiment, the plastic film has a thickness of about 0.01 mm to 0.5 mm. In another embodiment, the plastic film has a thickness of about 0.01 mm to 0.45 mm. In another embodiment, the plastic film has a thickness of about 0.05 mm to 0.45 mm. In another embodiment, the plastic film has a thickness of about 0.05 mm to 0.4 mm. In another embodiment, the plastic film has a thickness of about 0.1 mm to 0.4 mm. In another embodiment, the plastic film has a thickness of about 0.1 mm to 0.35 mm. In another embodiment, the plastic film has a thickness of about 0.15 mm to 0.35 mm. In another embodiment, the plastic film has a thickness of about 0.15 mm to 0.3 mm. In another embodiment, the plastic film has a thickness of about 0.2 mm to 0.25 mm.

In another embodiment, the kit comprises an adhesive sheet. In another embodiment, the adhesive sheet comprises an adhesive component selected from the following: acrylic emulsion, a solvent-based acrylic and an acrylic hot melt adhesive.

In another embodiment, the kit comprises a decorative template that covers one or more regions of the body area. In another embodiment, the decorative template limits application of the composition and/or the fragrance-releasing complex to those regions of the body area not covered by the decorative template. In another embodiment, the body area is selected from the group comprising skin, nails, teeth, and any combination thereof. In another embodiment, the kit is for home use. In one embodiment, the present invention provides a kit for decorating a body surface with a composition or a complex as described herein. In one embodiment, the present invention provides a kit wherein the composition and/or the fragrance-releasing complex further comprise a pigment.

EXAMPLES

The experiments conducted with the below formulations/ compositions involved applying 6 ml of each composition to the arm of an adult female. The fragrance duration experiments involved applying 6 ml of the below compositions to a designated glass surface.

All fragrance related tests were performed by one of the inventors who smelled the compositions in a close room at 25° C. by placing her nose 5 cm from the composition.

Fragrance duration tests were performed every 4 hours until 20 hours and every hour from 20 hours to 30 hours.

The intensity of immediate Fragrance release was measured 1 minute after the composition was applied to an adult skin. The fragrance intensity was given a score from 1 to 10, wherein 1 is minimal fragrance and 10 is maximal fragrance.

The stability of the compositions was examined 30 minutes after each composition was applied to an adult female in a close room at 25° C.

The perfume used was a mixture of natural essential oils with aromatic chemicals. The perfume was insoluble in water, and soluble in alcohol. The perfume's refractive index is 1.4830 to 1.4970 and its gravity is 0.920 to 1.060.

The emulsifier used for these experiments was POLYSORBATE 80 (POE 20 sorbitan monoleate, SABO).

The pigments used were: 1. IRID-100, Mica coated with metallic oxides/tin dioxides, (manufactured by Pritty); 2. Aluminum Powder; 3. Bronze Powder; 4. Copper Powder; and mixtures of 2-4. Pigments 2-4 were purchased from ECKART GmbH. Additional pigments No effect to the pigment type was recorded.

Several organic polymers including modified starch polymers, calcium carbonate containing polymers, cellulose and its derivatives polymers, and mixture polymers were tested with the ingredients of the compositions of the invention. All the above tested polymers cause dispersion insufficiencies, instability, fragrance inhibition properties, skin incompatibility and other deleterious effects.

The effective polymer that was utilized is ALBERDINGK® AC 548 (manufactured by Alberdingk Boley GmbH). The polymer is aqueous, fine disperse, medium viscous, APEO-free copolymer-dispersion of acrylic and methacrylic acid esters and without plasticizers. It includes from 49-51% solids and has a pH value of 7.5-8.5. It has viscosity of 3000-6000 mPas, density of 1.07 g/cm$^3$, ultimate tensile strength of 9 N/mm$^2$, elongation at break of 500%, and E-Modulus of 2 N/mm$^2$.

EXAMPLES

Example 1: 12 Selected Formulations of the Invention 12 different formulas of the invention were applied to the skin around the arm of an adult user. The water based copolymer-dispersion of acrylic and methacrylic acid esters was previously selected as it provided short drying/stabilization period and sufficient elasticity. Likewise, a clay thickener was chosen as it stabilized the emulsion, optimized it rheological behavior, its homogeneity, enhanced drying and increased elasticity.

3 different clay thickeners were tested and the most dense clay thickener proved to provide superior in-vivo results. As can be clearly viewed from table 1, the concentration of the 603 thickener has direct impact on drying time.

A drying period of 15 to 30 seconds is optimal. Therefore the formulations having an optimal drying period were further developed.

Interestingly, the smell and the intensity of the fragrance did not change within the various tested formulation and seemed to be solely dependent on the perfume used and the concentration.

The results provided in table 1 clearly indicate that lack of a thickener and/or insufficient polymer concentration result in a pealing effect of the composition within up to 5 minutes The thickener influenced the quality of film on skin and drying time.

As stated above clay based thickeners were previously selected due to their superior stability, and rheological properties, also, size of particles the morphology, diffusion in solution.

Thickener 600 is CLiQFLOW 600 has solids content of ca. 100%, specific gravity of: ca. 2.5, and particle size of: 98%<53 microns (CLiQ SwissTech (Deutschland) GmbH).

Thickener 602 is CLiQFLOW 602 has active content of: 100% and density (20° C.) of: 1.0 g/cm$^3$ (CLiQ SwissTech (Deutschland) GmbH).

Thickener 603 is CLiQFLOW 603 CLiQFLOW 603 has active content of: 100% and density (20° C.) of: 1.6 g/cm$^3$ (CLiQ SwissTech (Deutschland) GmbH). The 603 includes bentonite clay and is modified with cellulose. Thus rheological properties, size of particles, the diffusion within solution are important factors for a successful product of the invention. thickener having a density of at least 1.0 g/cm$^3$ was required to maintain the integrity of the present composition after it was applied to the skin. It should be noted that only the combination of sufficient amount of polymer together with a clay dense thickener result in sufficient, immediate fragrance release, and skin stability upon drying.

"CF 603"

TABLE 1

| By weight percent | Formula # | Type of thickener | The intensity of immediate Fragrance release (1-10) | Quality of the film 30 minutes after it was applied to the skin | Film formation |
|---|---|---|---|---|---|
| | 1 | | | | |
| 40% | Polymer | | 7 | Few short cracks | yes |
| 30% | Pigment | | | | |
| 2% | Thickener | 603 | | | |
| 1% | Emulsifier | | | | |
| 20% | Water | | | | |
| 7% | Fragrance | | | | |
| | 2 | | | | |
| 50% | Polymer | | 9 | Very few short cracks | yes |
| 20% | Pigment | | | | |
| 1% | Thickener | 603 | | | |
| 1% | Emulsifier | | | | |
| 20% | Water | | | | |
| 8% | Fragrance | | | | |

TABLE 1-continued

| By weight percent | Formula # | Type of thickener | The intensity of immediate Fragrance release (1-10) | Quality of the film 30 minutes after it was applied to the skin | Film formation |
|---|---|---|---|---|---|
| | 3 | | | | |
| 63% | Polymer | | 7 | No Cracks | yes |
| 10% | Pigment | | | | |
| 1% | Thickener | 603 | | | |
| 1% | Emulsifier | | | | |
| 20% | Water | | | | |
| 5% | Fragrance | | | | |
| | 4 | | | | |
| 71% | Polymer | | 7 | No Cracks | yes |
| 10% | Pigment | | | | |
| 1% | Thickener | 603 | | | |
| 1% | Emulsifier | | | | |
| 10% | Water | | | | |
| 8% | Fragrance | | | | |
| | 5 | | | | |
| 60% | Polymer | | 8 | Small cracks | yes |
| 20% | Pigment | | | | |
| 0% | Thickener | | | | |
| 2% | Emulsifier | | | | |
| 10% | Water | | | | |
| 8% | Fragrance | | | | |
| | 6 | | | | |
| 60% | Polymer | | 8 | Small cracks | yes |
| 15% | Pigment | | | | |
| 0% | Thickener | | | | |
| 1% | Emulsifier | | | | |
| 15% | Water | | | | |
| 8% | Fragrance | | | | |
| | 7 | | | | |
| 60% | Polymer | | 9 | No Cracks | yes |
| 20% | Pigment | | | | |
| 1% | Thickener | 603 | | | |
| 1% | Emulsifier | | | | |
| 8% | Water | | | | |
| 10% | Fragrance | | | | |
| | 8 | | | | |
| 30% | Polymer | | 10 | No film | no |
| 30% | Pigment | | | | |
| 1% | Thickener | 603 | | | |
| 1% | Emulsifier | | | | |
| 8% | Water | | | | |
| 30% | Fragrance | | | | |
| | 9 | | | | |
| 55% | Polymer | | 8 | Many cracks and peelings | yes |
| 30% | Pigment | | | | |
| 5% | Thickener | 602 | | | |
| 1% | Emulsifier | | | | |
| 8% | Water | | | | |
| 10% | Fragrance | | | | |
| | 10 | | | | |
| 55% | Polymer | | 8 | Many cracks | yes |
| 30% | Pigment | | | | |
| 2% | Thickener | 602 | | | |
| 1% | Emulsifier | | | | |
| 8% | Water | | | | |
| 10% | Fragrance | | | | |
| | 11 | | | | |
| 55% | Polymer | | 9 | Many cracks and peelings | yes |
| 30% | Pigment | | | | |
| 1% | Thickener | 600 | | | |
| 1% | Emulsifier | | | | |
| 8% | Water | | | | |
| 10% | Fragrance | | | | |

TABLE 1-continued

| By weight percent | Formula # | Type of thickener | The intensity of immediate Fragrance release (1-10) | Quality of the film 30 minutes after it was applied to the skin | Film formation |
|---|---|---|---|---|---|
| | 12 | | | | |
| 20% | Polymer | | 8 | Many cracks and peelings | yes |
| 30% | Pigment | | | | |
| 1% | Thickener | 600 | | | |
| 1% | Emulsifier | | | | |
| 40% | Water | | | | |
| 8% | Fragrance | | | | |

In summary, it seems that the actual presence of a thickener and particularly thickener 603 having an elevated density of 1.6 g/cm$^3$ and at least 50% polymer confer proper stability together with fragrance retention and release as evidenced in formulations: 3-6 and 7 which were chosen for additional testing and assessments. Interestingly insufficient amount of polymer inhibited film formation.

Example 2: Formulation Drying Time and Stability

Obviously optimal drying time is crucial to the success of a formulation of the invention. A very short drying time such as 15 seconds and less may render a kit of the invention unusable as the formulation will dry within the applicator and prior to applying it to the skin. A long drying time will render a composition of the invention as a stain hazard.

Likewise, it is essential that a stable smell or fragrance will remain during at least 12 hours from applying the formulation to a body surface.

Table 2 summarizes the impact of the amount and type of thickener and the amount of polymer on the drying time and stability (fragrance release duration and physical integrity) of the 12 formulations presented in table 2.

TABLE 2

| By weight percent | Formula # | Type of thickener | Duration of continuous Fragrance release (hours) | Film Quality of film | Reaching film skin stability from the time of application (seconds) at room temperature |
|---|---|---|---|---|---|
| | 1 | | | | |
| 40% | Polymer | | 23 | Few cracks | 15 |
| 30% | Pigment | | | | |
| 2% | Thickener | 603 | | | |
| 1% | Emulsifier | | | | |
| 20% | Water | | | | |
| 7% | Fragrance | | | | |
| | 2 | | | | |
| 50% | Polymer | | 24 | Minor peeling | 19 |
| 20% | Pigment | | | | |
| 1% | Thickener | 603 | | | |
| 1% | Emulsifier | | | | |
| 20% | Water | | | | |
| 8% | Fragrance | | | | |
| | 3 | | | | |
| 63% | Polymer | | 20 | Stable | 19 |
| 10% | Pigment | | | | |
| 1% | Thickener | 603 | | | |
| 1% | Emulsifier | | | | |
| 20% | Water | | | | |
| 5% | Fragrance | | | | |
| | 4 | | | | |
| 71% | Polymer | | 25 | Stable | 16 |
| 10% | Pigment | | | | |
| 1% | Thickener | 603 | | | |
| 1% | Emulsifier | | | | |
| 10% | Water | | | | |
| 8% | Fragrance | | | | |
| | 5 | | | | |
| 60% | Polymer | | 24 | Single crack | 40 |
| 20% | Pigment | | | | |
| 0% | Thickener | 603 | | | |
| 2% | Emulsifier | | | | |
| 10% | Water | | | | |
| 8% | Fragrance | | | | |

TABLE 2-continued

| By weight percent | Formula # | Type of thickener | Duration of continuous Fragrance release (hours) | Film Quality of film | Reaching film skin stability from the time of application (seconds) at room temperature |
|---|---|---|---|---|---|
| | 6 | | | | |
| 60% Polymer<br>15% Pigment<br>0% Thickener<br>1% Emulsifier<br>15% Water<br>8% Fragrance | | 603 | 24 | Single crack | 38 |
| | 7 | | | | |
| 60% Polymer<br>20% Pigment<br>1% Thickener<br>1% Emulsifier<br>8% Water<br>10% Fragrance | | 603 | 30 | Stable | 20 |
| | 8 | | | | |
| 30% Polymer<br>30% Pigment<br>1% Thickener<br>1% Emulsifier<br>8% Water<br>30% Fragrance | | 603 | 34 | Many cracks and peelings | 30 |
| | 9 | | | | |
| 55% Polymer<br>30% Pigment<br>5% Thickener<br>1% Emulsifier<br>8% Water<br>10% Fragrance | | 602 | 30 | Many cracks and peelings | 25 |
| | 10 | | | | |
| 55% Polymer<br>30% Pigment<br>2% Thickener<br>1% Emulsifier<br>8% Water<br>10% Fragrance | | 602 | 30 | Many cracks and peelings | 35 |
| | 11 | | | | |
| 55% Polymer<br>30% Pigment<br>1% Thickener<br>1% Emulsifier<br>8% Water<br>10% Fragrance | | 600 | 30 | Many cracks and peelings | 30 |
| | 12 | | | | |
| 20% Polymer<br>30% Pigment<br>1% Thickener<br>1% Emulsifier<br>40% Water<br>8% Fragrance | | 600 | 24 | Many cracks and peelings | 40 |

Interestingly, table 2 unexpectedly further demonstrates that a stable composition should include at least 50% and even 60% polymer and a clay based thickener having a high density as provided in example 1. With respect to the duration of continuous fragrance release (hours), all formulation where effective in maintain a solid fragrance for at least 15 hours as required. Interestingly, the amount of fragrance or water did not directly correlate with: (a) the duration of fragrance release and/or the intensity of immediate fragrance release; and (b) the physical stability of the dried composition—the skin decoration. Thus, the 603 thickener, at least 5% fragrance, and over 50% polymer render the present composition effective in providing a novel smell releasing body decoration system.

What is claimed is:

1. A composition comprising: (i) 7 to 30% by weight a fragrance; (ii) an acrylic polymer; (iii) 0.2 to 2%, by weight, thickener; (iv) an emulsifier; (v) an aqueous solution, and (vi) a pigment, wherein said thickener has a density of 0.7 to 2 g/cm$^3$ at 20° C.

2. The composition of claim 1, wherein said composition is a visible light fragrance-releasing complex.

3. The composition of claim 1, wherein a noticeable amount of fragrance is released for at least 15 hours.

4. The composition of claim 1, wherein, said emulsifier is in an amount of from 0.2 to 2% by weight.

5. The composition of claim 1, wherein said aqueous solution is in an amount of from 2 to 20% by weight, said pigment is in an amount of from 5 to 40% by weight or both.

6. The composition of claim 1, wherein said emulsifier is a nonionic emulsifier.

7. The composition of claim 1, wherein said acrylic polymer is within an emulsion.

8. The composition of claim 1, wherein said fragrance comprises: an alcohol, an ether, a nitrile, an aldehyde, an ester, a ketone, a lactone, a thiol, an amine, a schiff-base, a terpene, a cyclic alkene, a cyclic oxide, an oxime, an essential oil, an aromatic species, or any combination thereof.

9. The composition of claim 1, wherein said fragrance comprises: i) a base note fragrance; ii) a middle note fragrance; iii) a top note fragrance; iv) a balance carrier; v) a fixative, or any combination thereof.

10. The composition of claim 1, wherein said fragrance comprises a volatile fragrance.

11. The composition of claim 1, wherein said fragrance is encapsulated or entrapped within said acrylic polymer.

12. The composition of claim 1, retaining a perceptible fragrance for at least seven days.

13. The composition of claim 1, wherein said acrylic polymer has a viscosity of 1500 to 12000 mPas at 20° C.

14. The composition of claim 1, wherein said acrylic polymer has a density of 0.5 to 2 $g/cm^3$ at 20° C.

15. A method for conferring, enhancing, improving or modifying the odor properties of a body surface, comprising contacting or treating said body surface with said composition of claim 1.

16. The method of claim 15, further comprising decorating said body surface.

17. A kit for applying a fragrance to a subject, comprising the composition of claim 1; and means for topically applying said composition to a body surface.

18. The kit of claim 17, wherein said applying said composition is applying a body decoration.

* * * * *